US007094603B2

(12) United States Patent
Lawman et al.

(10) Patent No.: US 7,094,603 B2
(45) Date of Patent: Aug. 22, 2006

(54) MATERIALS AND METHODS FOR TREATING ONCOLOGICAL DISEASE

(75) Inventors: Michael J. P. Lawman, Tampa, FL (US); Patricia Lawman, Tampa, FL (US)

(73) Assignee: Morphogenesis, Inc., Tampa, FL (US)

( * ) Notice: Subject to any disclaimer, the term of this patent is extended or adjusted under 35 U.S.C. 154(b) by 324 days.

(21) Appl. No.: 10/652,578

(22) Filed: Aug. 29, 2003

(65) Prior Publication Data
US 2004/0142464 A1 Jul. 22, 2004

Related U.S. Application Data

(63) Continuation of application No. 09/950,374, filed on Sep. 10, 2001, now abandoned, which is a continuation of application No. 09/394,226, filed on Sep. 13, 1999, now abandoned, which is a continuation of application No. PCT/US99/00787, filed on Jan. 14, 1999.

(60) Provisional application No. 60/071,497, filed on Jan. 14, 1998, now abandoned.

(51) Int. Cl.
C12B 15/83 (2006.01)
C12B 15/85 (2006.01)
C12N 5/00 (2006.01)
C12N 5/02 (2006.01)
C12N 5/06 (2006.01)

(52) U.S. Cl. .................. 435/455; 435/325; 435/366
(58) Field of Classification Search ............. 435/320.1, 435/325, 455, 456, 366
See application file for complete search history.

(56) References Cited

U.S. PATENT DOCUMENTS 5,736,388 A 4/1998 Chada et al.
2002/0193571 A1* 12/2002 Carter et al. ............. 530/387.3

FOREIGN PATENT DOCUMENTS

| EP | 0569678 | 11/1993 |
|---|---|---|
| WO | WO 93/24136 | 12/1993 |
| WO | WO 94/21808 | 9/1994 |
| WO | WO 95/00178 | 1/1995 |
| WO | WO 95/13092 | 5/1995 |
| WO | WO 96/29093 | 9/1996 |
| WO | WO 96/36366 | 11/1996 |

OTHER PUBLICATIONS

Avery, A. C. et al. "Activation of T Cells by Superantigen in Class II-Negative Mice" *J. Immunol.*, 1994, pp. 4855-4861, vol. 153.
Banchereau, J. et al., "Dendritic Cells and the Control of Immunity" *Nature*, 1998, pp. 245-252, vol. 392.
Barratt-Boyes, S. M. et al. "Studies in a Chimpanzee Model of Dendritic Cell-Based Cancer Vaccines", Proceedings of the 87th, Annual Meeting of the American Association for Cancer, 1996, XP002039146 (abstract only).
Boyle, Michael D. P. et al. "Analysis of Genes Encoding Two Unique Type IIa Immunoglobulin G-Binding Proteins Expressed by a Single Group a Streptococcal Isolate" *Infection and Immunology*, 1994, pp. 1336-1347, vol. 62, No. 4.
Boyle, Michael D. P. et al. "Characterization of A Gene Coding for A Type IIo Bacterial IgG-Binding Protein" *Molecular Immunology*, 1995, pp. 669-678, vol. 32, No. 9.
Dellabona, Paolo et al. "Superantigens Interact With MHC Class II Molecules Outside of the Antigen Groove" *Cell*, 1990, pp. 1115-1121, vol. 62.
Dohlsten, M. et al. "Monoclonal Antibody-Targeted Superantigens: A Different Class of Anti-Tumor Agents" *Proc. Natl. Acad. Sci. USA*, 1991, pp. 9287-9291, vol. 88.
Dohlsten, M. et al. "Human Major Histocompatibility Complex Class II-Negative Colon Carcinoma Cells Present Staphylococcal Superantigens to Cytotoxic T Lymphocytes: Evidence for a Novel Enterotoxin Receptor" *Eur. J. Immunol.*, 1991, pp. 1229-1233, vol. 21.
Dohlsten, M. et al. "Role of the Adhesion Molecule ICAM-1 (CD54) in Staphylococcal Enterotoxin-Mediated Cytotoxicity" *Eur. J. Immunol.*, 1991, pp. 131-135, vol. 21.
Fleisher, B. et al. "T-Lymphocyte Stimulation by Microbial Superantigens" *Chem. Immunol.*, 1992, pp. 36-64 vol. 55.
Fraser, James D. et al. "CD28 and T Cell Antigen Receptor Signal Transduction Coordinately Regulate Interleukin 2 Gene Expression In Response to Superantigen Stimulation" *J. Ex. Med.*, 1992, pp. 1131-1134, vol. 175.

(Continued)

*Primary Examiner*—Brian Whiteman
(74) *Attorney, Agent, or Firm*—Edwards Angell Palmer & Dodge LLP

(57) ABSTRACT

Novel methods are disclosed for treating oncological disorders in an individual or animal using a superantigen expressed in tumor cells. A gene encoding a superantigen, such as an M-like protein of group A streptococci, can be introduced into a tumor cell in order to make the tumor cell more immunogenic in the host. Also contemplated are methods wherein a cell expresses a superantigen or superantigens, and immunogenic or immunostimulatory proteins, such as foreign MHC, cytokines, porcine-derived hyperacute rejection antigen, *Mycobacterium*-derived antigens, and the like. The subject invention also pertains to cells transformed with polynucleotides encoding a superantigen and foreign MHC antigen, cytokines, and other immunogenic or immunostimulatory proteins. Transformed cells according to the subject invention are then provided to an individual or animal in need of treatment for an oncological disorder. The immune response to tumor cells transformed according to the present invention inhibits in vivo tumor growth and results in subsequent tumor regression. The subject invention also pertains to cell lines transformed with genes encoding a superantigen and, optionally, a foreign Class II MHC antigen and/or a cytokine.

15 Claims, 7 Drawing Sheets

OTHER PUBLICATIONS

Gilboa, Eli et al. "Immunotherapy of Cancer With Dendritic-Cell-Based Vaccines" *Cancer Immunol Immunother*, 1998, pp. 82-87, vol. 46, No. 2.

Hartwig, Udo F. et al. "Mutations Affecting MHC Class II Binding of the Superantigen Streptococcal Erythrogenic Toxin A" *International Immunology*, 1993, pp. 869-875, vol. 5, No. 8.

Herman, Andrew et al. "Identification of the Staphylococcal Enterotoxin A Superantigen Binding Site in the β1 Domain of the Human Histocompatibility Antigen HLA-DR", *Proc. Natl. Acad. Sci. USA*, 1991, pp. 9954-9958, vol. 88.

Hermann, Thomas et al. "Staphylococcal Enterotoxin-Dependent Lysis of MHC Class II Negative Target Cells by Cytolytic T Lymphocytes", *J. Immunol.*, 1991, pp. 2504-2512, vol. 146.

Hock, Randy A. et al. "Murine Neuroblastoma Vaccines Produced by Retroviral Transfer of MHC Class II Genes", *Cancer Gene Therapy*, 1996, pp. 314-320, vol. 3, No. 5.

Johnson, Howard M. et al. "Superantigens in Human Disease", *Scientific American*, 1992, pp. 92-111.

Karp, David R. et al. "The α1 Domain of the HLA-DR Molecule is Essential for High-Affinity Binding of the Toxic Shock Syndrome Toxin-1", *Nature*, 1990, pp. 474-476, vol. 346.

Menard, S. et al. "Mycobacterium Tuberculosis Gene Transfer in Melanoma Cells Induces Antitumoral Immunity in Mice" *Cancer Gene Therapy*, 1995, p. 318, vol. 2, No. 4.

Mayordoma, J.I. et al. "Bone Marrow-Derived Dendritic Cells Pulsed With Synthetic Tumour Peptides Elicit Protective and Therapeutic Antitumour Immunity", *Nature Medicine*, 1995, pp. 1297-1302, vol. 1, No. 12.

Mollick, Joseph A. et al. "Staphylococcal Exotoxin Activation of T Cells", *J. Immunology*, 1991, pp. 463-468, vol. 146.

Panina-Bordignon, Paola et al. "Identification of HLA-DRα Chain Residues Critical for Binding of the Toxic Shock Syndrome Toxin Superantigen", *J. Exp. Med.*, 1992, pp. 1779-1784, vol. 176.

Rust, Chantal, J.J. et al. "Specific Recognition of Staphylococcal Enterotoxin A by Human T Cells Bearing Receptors With the $V_{65}9$ Region", *Nature*, pp. 572-574, vol. 346.

Webb, Susan R. et al. "T-cell Activation by Superantigens", *Curr Opinion in Immun.*, 1994, pp. 467-475, vol. 6.

Tomai, M. et al. "Superantigenicity of Streptococcal M Protein", *J. Exp. Med.*, 1990, pp. 359-362, vol. 172.

Fleischer, B. et al. "Superantigens and Pseudosuperantigens of Gram-Positive Cocci", *Med. Microbiol. Immumol.*, 1995, pp. 1-8, vol. 184.

Degnan, B. et al. "*Streptococcus pyogenes* Type 5 M Protein is an Antigen, Not a Superantigen, for Human T Cells", *Human Immunology*, 1997, pp. 206-215, vol. 53.

Esaki, Y. et al. "Role of Human Major Histocompatibility Complex DQ Molecules in Superantigenicity of *Streptococcus*-Derived Protein", *Infection and Immunity*, 1994, p. 1228-1235, vol. 62, No. 4.

Anderson, W.F. "Human Gene Therapy", *Nature*, 1998, pp. 25-30, vol. 392(Supp.).

Verma, I. M. et al. "Gene Therapy—Promises, Problems and Prospects", *Nature*, 1997, pp. 239-242, vol. 389.

Gomez-Navarro, J. et al. "Gene Therapy for Cancer", *Eur. J. Cancer*, 1999, pp. 867-885, vol. 35, No. 6.

Ngo, J. T. et al. "Computational Complexity, Protein Structure Prediction, and the Levinthal Paradox", *The Protein Folding Problem and Tertiary Structure Prediction*, 1994, pp. 433 and 492-495, Merz (ed.) Birkhauser, Boston, MA.

Chiu, T-L. et al. "Optimizing Energy Potentials for Success in Protein Tertiary Structure Prediction", *Folding & Design*, May 1998, pp. 223-228, vol. 3.

Orkin, S. H. et al. "Report and Recommendations of the Panel to Assess the NIH Investment in Research on Gene Therapy", Dec. 1995, pp. 1-41.

Ross, G. et al. "Gene Therapy in the United States: A Five Year Status Report", *Human Gene Therapy*, Sep. 1996, pp. 1781-1790, vol. 7.

Ostrand-Rosenberg, S. et al. "Tumor-Specific Immunity Can Be Enhanced by Transfection of Tumor Cells with Syngeneic MHC-Class-II Genes or Allogeneic MHC-Class-I Genes", *Int. J. Cancer*, 1991, pp. 61-68, vol. 6.

Kalland, T. et al. "Targeting of Superantigens", *Cell Biophysics*, 1993, pp. 147-164, vol. 22.

Coupar, B. E. H. et al. "A General Method for the Construction of Recombinant Vaccinia Viruses Expressing Multiple Foreign Genes", *Gene*, 1988, pp. 1-10, vol. 68.

Eck, S. L. et al. "Scope of Gene Therapy", *Gene-Based Therapy*, pp. 77-101, Chapter 5.

Marshall, E. "Gene Therapy's Growing Pains", *Science*, Aug. 1995, pp. 1050-1055, vol. 269.

Hollingshead, S. K. et al. "Molecular of a Multigene Family in Group A Streptococci", *Mol. Biol. Evol.*, 1994, pp. 208-219, vol. 11, No. 2.

Hollingshead, S. K. et al. "Structural Heterogeneity of the Emm Gene Cluster in Group A Streptococci", *Mol. Microbiol.*, May 1993, pp. 707-717, vol. 8, No. 4.

Ji, Y. et al. "Intranasal Immunization with C5a Peptidase Prevents Nasopharygeal Colonization of Mice by the Group A *Streptococcus", Infection and Immunity*, Jun. 1997, pp. 2080-2087, vol. 65, No. 6.

Bessen, D. et al. "Passive Acquired Mucosal Immunity to Group A Streptococci by Secretory Immunoglobulin A", *J. Exp. Med.*, Jun. 1988, pp. 1945-1950, vol. 167, No. 6.

* cited by examiner

```
Consensus           CTGTGGAATG TGTGTCAGTT AGGGTGTGGA AAGTCCCCAG GCTCCCCAGC    50
emml55/pSVK3        CTGTGGAATG TGTGTCAGTT AGGGTGTGGA AAGTCCCCAG GCTCCCCAGC    50

Consensus           AGGCAGAAGT ATGCAAAGCA TGCATCTCAA TTAGTCAGCA ACCAGGTGTG   100
emml55/pSVK3        AGGCAGAAGT ATGCAAAGCA TGCATCTCAA TTAGTCAGCA ACCAGGTGTG   100

Consensus           GAAAGTCCCC AGGCTCCCCA GCAGGCAGAA GTATGCAAAG CATGCATCTC   150
emml55/pSVK3        GAAAGTCCCC AGGCTCCCCA GCAGGCAGAA GTATGCAAAG CATGCATCTC   150

Consensus           AATTAGTCAG CAACCATAGT CCCGCCCCTA ACTCCGCCCA TCCCGCCCCT   200
emml55/pSVK3        AATTAGTCAG CAACCATAGT CCCGCCCCTA ACTCCGCCCA TCCCGCCCCT   200

Consensus           AACTCCGCCC AGTTCCGCCC ATTCTCCGCC CCATGGCTGA CTAATTTTTT   250
emml55/pSVK3        AACTCCGCCC AGTTCCGCCC ATTCTCCGCC CCATGGCTGA CTAATTTTTT   250

Consensus           TTATTTATGC AGAGGCCGAG GCCGCCTCGG CCTCTGAGCT ATTCCAGAAG   300
emml55/pSVK3        TTATTTATGC AGAGGCCGAG GCCGCCTCGG CCTCTGAGCT ATTCCAGAAG   300

Consensus           TAGTGAGGAG GCTTTTTTGG AGGCCTAGGC TTTTGCAAAA AGCTATCGAA   350
emml55/pSVK3        TAGTGAGGAG GCTTTTTTGG AGGCCTAGGC TTTTGCAAAA AGCTATCGAA   350
second sec (1-178)                                         TTTGCAAAA AGCTATCGAA    19

Consensus           TTAATACGAC TCATTATAGG GAGATCGAAT TCGGCWTGGC TAAAAATACC   400
emml55/pSVK3        TTAATACGAC TCATTATAGG GAGATCGAAT TC---ATGGC TAAAAATACC   400
second sec (1-178)  TTAATACGAC TCATTATAGG GAGATCGAAT TCGGCTTGGC TAAAAATACC    69

Consensus           ACGAATAGAC ACKATTCGCT TAGAAAATTA AAAACAGGAA CGGCTTCAGT   450
emml55/pSVK3        ACGAATAGAC ACGATTCGCT TAGAAAATTA AAAACAGGAA CGGCTTCAGT   450
second sec (1-178)  ACGAATAGAC ACTATTCGCT TAGAAAATTA AAAACAGGAA CGGCTTCAGT   119
```

FIG. 4A

```
Consensus         AGCAGTAGCT TTGACTGTTT TTGGGACAGG ACTGGTAGCA GGGCAGACAG   500
emm155/pSVK3      AGCAGTAGCT TTGACTGTTT TTGGGACAGG ACTGGTAGCA GGGCAGACAG   500
second sec (1-178) AGCAGTAGCT TTGACTGTTT TTGGGACAGG ACTGGTAGCA GGGCAGACAG   169

Consensus         TAAAAGCAAA CCAAACAGAA CCATCTCAGA CCAATAACAG ATTATATCAA   550
emm155/pSVK3      TAAAAGCAAA CCAAACAGAA CCATCTCAGA CCAATAACAG ATTATATCAA   550
second sec (1-178) TAAAAGCAA                                                219

Consensus         GAAAGACAAC GTTTACAGGA TTTAAAAAGT AAGTTTCAAG ACCTGAAAAA   600
emm155/pSVK3      GAAAGACAAC GTTTACAGGA TTTAAAAAGT AAGTTTCAAG ACCTGAAAAA   600

Consensus         TCGTTCAGAG GGATACATTC AGCAATACTA CGACGAAGAA AAGAACAGTG   650
emm155/pSVK3      TCGTTCAGAG GGATACATTC AGCAATACTA CGACGAAGAA AAGAACAGTG   650

Consensus         GAAGTAACTC TAACTGGTAC GCAACCTACT TAAAAGAATT AAATGACGAA   700
emm155/pSVK3      GAAGTAACTC TAACTGGTAC GCAACCTACT TAAAAGAATT AAATGACGAA   700

Consensus         TTTGAACAAG CTTATAATGA ACTTAGTGGT GATGGTGTAA AAAAATTAGC   750
emm155/pSVK3      TTTGAACAAG CTTATAATGA ACTTAGTGGT GATGGTGTAA AAAAATTAGC   750

Consensus         TGCAAGTTTG ATGGAAGAAA GAGTCGCTTT AAGAGACGAA ATCGATCAGA   800
emm155/pSVK3      TGCAAGTTTG ATGGAAGAAA GAGTCGCTTT AAGAGACGAA ATCGATCAGA   800

Consensus         TTATGAAAAT ATCAGAAGAA TTAAAAAATA AGCTGAGAGC AACAGAAGAA   850
emm155/pSVK3      TTATGAAAAT ATCAGAAGAA TTAAAAAATA AGCTGAGAGC AACAGAAGAA   850
```

FIG. 4B

SEQUENCE LISTING

```
<160> NUMBER OF SEQ ID NOS: 6

<210> SEQ ID NO 1
<211> LENGTH: 850
<212> TYPE: DNA
<213> ORGANISM: Streptococcus

<400> SEQUENCE: 1
ctgtggaatg tgtgtcagtt agggtgtgga aagtcccag gctcccagc aggcagaagt      60 atgcaaagca tgcatctcaa ttagtcagca accaggtgtg gaaagtcccc aggctcccca    120
gcaggcagaa gtatgcaaag catgcatctc aattagtcag caaccatagt cccgcccta    180
```

| | |
|---|---|
| actccgccca tcccgcccct aactccgccc agttccgccc attctccgcc ccatggctga | 240 |
| ctaattttt ttatttatgc agaggccgag gccgcctcgg cctctgagct attccagaag | 300 |
| tagtgaggag ctttttggg aggcctaggc ttttgcaaaa agctatcgaa ttaatacgac | 360 |
| tcattatagg gagatcgaat tcggcwtggc taaaaatacc acgaatagac ackattcgct | 420 |
| tagaaaatta aaaacaggaa cggcttcagt agcagtagct ttgactgttt ttgggcagg | 480 |
| actggtagca gggcagacag taaaagcaaa ccaaacagaa ccatctcaga ccaataacag | 540 |
| attatatcaa gaaagacaac gtttacagga tttaaaaagt aagtttcaag acctgaaaaa | 600 |
| tcgttcagag ggatacattc agcaatacta cgacgaagaa aagaacagtg gaagtaactc | 660 |
| taactggtac gcaacctact aaaagaatt aaatgacgaa tttgaacaag cttataatga | 720 |
| acttagtggt gatggtgtaa aaaaattagc tgcaagtttg atggaagaaa gagtcgcttt | 780 |
| aagagacgaa atcgatcaga ttatgaaaat atcagaagaa ttaaaaaata agctgagagc | 840 |
| aacagaagaa | 850 |

<210> SEQ ID NO 2
<211> LENGTH: 847
<212> TYPE: DNA
<213> ORGANISM: Streptococcus

<400> SEQUENCE: 2

| | |
|---|---|
| ctgtggaatg tgtgtcagtt agggtgtgga aagtccccag gctccccagc aggcagaagt | 60 |
| atgcaaagca tgcatctcaa ttagtcagca accaggtgtg aaagtcccc aggctcccca | 120 |
| gcaggcagaa gtatgcaaag catgcatctc aattagtcag caaccatagt cccgcccta | 180 |
| actccgccca tcccgcccct aactccgccc agttccgccc attctccgcc ccatggctga | 240 |
| ctaattttt ttatttatgc agaggccgag gccgcctcgg cctctgagct attccagaag | 300 |
| tagtgaggag ctttttggg aggcctaggc ttttgcaaaa agctatcgaa ttaatacgac | 360 |
| tcattatagg gagatcgaat tcatggctaa aaataccacg aatagacacg attcgcttag | 420 |
| aaaattaaaa acaggaacgg cttcagtagc agtagctttg actgttttg gacaggact | 480 |
| ggtagcaggg cagacagtaa agcaaaccaa acagaacca tctcagacca ataacagatt | 540 |
| atatcaagaa agacaacgtt tacaggattt aaaaagtaag tttcaagacc tgaaaaatcg | 600 |
| ttcagaggga tacattcagc aatactacga cgaagaaaag aacagtggaa gtaactctaa | 660 |
| ctggtacgca acctacttaa agaattaaa tgacgaattt gaacaagctt ataatgaact | 720 |
| tagtggtgat ggtgtaaaaa aattagctgc aagtttgatg gaagaaagag tcgctttaag | 780 |
| agacgaaatc gatcagatta tgaaaatatc agaagaatta aaaataagc tgagagcaac | 840 |
| agaagaa | 847 |

<210> SEQ ID NO 3
<211> LENGTH: 178
<212> TYPE: DNA
<213> ORGANISM: Streptococcus

<400> SEQUENCE: 3

| | |
|---|---|
| tttgcaaaaa gctatcgaat taatacgact cattatagg gagatcgaatt cggcttggct | 60 |
| aaaaatacca cgaatagaca ctattcgctt agaaaattaa aaacaggaac ggcttcagta | 120 |
| gcagtagctt tgactgtttt tgggacagga ctggtagcag ggcagacagt aaaagcaa | 178 |

<210> SEQ ID NO 4
<211> LENGTH: 31

-continued

```
<212> TYPE: DNA
<213> ORGANISM: Streptococcus

<400> SEQUENCE: 4
tagaattcat ggctaaaaat accacgaata g                                    31

<210> SEQ ID NO 5
<211> LENGTH: 32
<212> TYPE: DNA
<213> ORGANISM: Streptococcus

<400> SEQUENCE: 5
cagtttgcgt ttcttctttt gattgagctc tt                                   32

<210> SEQ ID NO 6
<211> LENGTH: 18
<212> TYPE: DNA
<213> ORGANISM: Streptococcus

<400> SEQUENCE: 6
cagttccgcc cattcttc                                                   18
```

MATERIALS AND METHODS FOR TREATING ONCOLOGICAL DISEASE

CROSS-REFERENCE TO A RELATED APPLICATIONS

This application is a continuation of U.S. application Ser. No. 09/950,374 filed Sep. 10, 2001, now abandoned, which is a continuation of U.S. application Ser. No. 09/394,226, filed Sep. 13, 1999, now abandoned, which is a continuation of International Application No. PCT/US99/00787, filed Jan. 14, 1999, which claims priority from U.S. provisional application Ser. No. 60/071,497, filed Jan. 14, 1998, now abandoned.

BACKGROUND OF THE INVENTION

While a place for somatic gene therapy in the treatment of inherited single gene disorders is no longer disputed, the potential of gene therapy for the treatment of malignancies may not be readily apparent. Because most forms of cancer have been shown to be complex, multifactorial, and multigenic in nature, there are many conceptual and technical obstacles which must be overcome in order to approach this disease at the genetic level. Yet, it is the molecular nature of tumorigenesis, i.e., the activation of dominant oncogenes and/or the inactivation of tumor suppressor genes, that provides insight for such strategies in that these genetic events represent novel targets for molecular therapy. Already, genetic analysis is being used in diagnostic and prognostic predictions in certain malignancies (e.g., amplification of erb-B2 in breast and ovarian cancer; amplification of N-myc in neuroblastoma; and ras mutations in adenocarcinoma of the lung).

At present, there are two general strategies for gene therapy: gene augmentation and gene replacement. Gene augmentation or gene addition is simply the introduction of foreign genetic sequences into a cell. Usually this means the insertion of a normal copy of a particular gene into a cell expressing a mutant form of that gene. In many cases, the addition of functional genetic information has been used successfully to restore a genetic function in these defective cells. However, in other cases, the addition of a normal gene is not sufficient to repair the abnormality because this technique does not remove or correct the resident, nonfunctional mutant gene. Furthermore, the random insertion of foreign sequences into nonspecific sites of the genome may result in mutagenic events such as insertional inactivation of genes necessary for the viability of that cell, or uncontrolled regulation of the transgene and/or flanking chromosomal sequences. In these instances it will be necessary to modify specific gene sequences by targeted gene replacement, i.e., site-specific recombination of foreign DNA into targeted genomic sequences. Each of these approaches have applications in gene therapy for cancer.

The immune system has demonstrated the potential to play a protective role in cancer. However, the vast majority of malignancies arise in immunocompetent hosts. Although cellular activity is normally regulated by the various protein kinases, growth factors, growth factor receptors, and DNA binding proteins encoded by proto-oncogenes, together with genes that can suppress malignant transformation, such as the retinoblastoma and p53 genes, if one or more of these genes is or becomes defective, it can result in a clone with an abnormal pattern of growth control. The fact that such a clone grows uncontrolled in an individual, indicates that the immune system has either failed to recognize tumor-specific antigens or has failed to effectively respond. Transgenic immunotherapy, an important arm of somatic gene therapy for cancer, aims at strengthening the immune surveillance of the body.

It is known that the presence of cytokines at the site of a tumor can drastically alter tumor/host relations. In some cases a highly destructive and specific response to otherwise nonimmunogenic tumors can be elicited by the insertion of genes encoding cytokines (e.g., interleukin-2, interleukin-4, interferon-γ, and tumor necrosis factor) into tumor cells which are then used as "tumor vaccines." Anti-tumor responses can also be enhanced by the transfection of these genes into cytotoxic lymphocytes or macrophages. Autologous tumor-infiltrating lymphocytes have been used successfully in such genetic immunomodulation studies because of their inherent specificity for the tumor, and their ability to home back to the tumor site when reinfused into the patient. This approach has been termed "adoptive immunotherapy." It is also possible to protect normal tissue by stably transfecting normal bone marrow cells with cytokine genes prior to chemotherapy, thereby achieving a more continuous effect while obviating the need to infuse these drugs which have short half-lives and produce systemic side effects when delivered intravenously.

Despite the widespread use of chemotherapeutic agents for the treatment of solid tumors, efficacy has been restricted by their toxicity to normal cells. Transfection of normal stem cells with transgenes conferring resistance to these agents would result in cytotoxic drug-resistant cells and allow the administration of more therapeutically significant doses. Another type of gene therapy that is gaining momentum and which is now in clinical trails is the use of "informational drugs." Antisense oligonucleotides, small synthetic nuclease-resistant nucleotide sequences complementary to specific RNA sequences, are perhaps the best known example of this. By specifically binding and thereby inhibiting transcription and/or translation of a single oncogene, it may be possible to reverse clinical symptoms.

It is well established that T lymphocytes recognize two different types of antigens, one being peptides derived from conventional protein antigens and the other being superantigens. The classical model for superantigen activity suggests that the superantigens react in some ways like conventional antigens but exhibit critical differences in others (Johnson et al., 1992). Before a T helper cell can recognize conventional protein antigens, these proteins must first undergo processing by macrophages or other antigen presenting cells (APC). APCs then display the peptide on the cell surface in combination with MHC. Unlike typical antigens, however, superantigens bind MHC directly without uptake and processing by APCs (Johnson et al., 1992).

Unlike conventional antigens, where recognition by T cells involves both variable elements of the α and β chains of TCR, superantigen recognition depends primarily on the TCR Vβ region. Also, unlike ordinary antigens, superantigens bind to specific Vβ segments of TCR which are outside of the normal antigen-binding groove. This binding occurs regardless of the remaining structure of the TCR. These interactions lead to strong Vβ-specific T cell activation (Dellabona et al., 1990, and Rust et al., 1990). Furthermore, because the number of different types of Vβ segments is small compared with the number of α, β receptors, many more T cells are capable of recognizing a particular superantigen than are able to identify a specific antigen (Herman et al., 1991).

The classical model of superantigen activity has since been revised. New observations suggest that there are additional interactions between the TCR and MHC molecules during superantigen engagement and this can have a significant impact on superantigen specificity and function (Webb and Gascoigne, 1994). For example, some studies show that it is not only Vβ, but also the α chain of the TCR which plays a role in the recognition of superantigens (Karp et al., 1990, and Panina et al., 1992). Furthermore, the MHC molecule does not function as an inert platform for superantigen presentation, but plays a role in T cell activation by superantigens. Some studies indicate that individual T cell clones are able to distinguish superantigens presented on MHC molecules with different specificity. Some murine T cell hybridomas can recognize superantigens in context of two different MHC molecules (Mollick et al., 1991; Hartwig and Fleischer, 1993). The revised model assumes that the molecular mechanism of T cell stimulation is probably a multivalent cross-linking of the TCR with MHC molecules. Additional adhesion molecules such as CD 2, LFA-1 or CD 28, may play a role during T cell stimulation (Fleischer and Hartwig, 1992, and Fraser et al., 1992). Another interesting observation suggests that in spite of the requirement for MHC class II molecules in T cell stimulation, there is evidence that superantigens interact with TCRs directly, in the absence of class II molecules. Binding to MHC II is not a prerequisite for T cell activation as superantigen-mediated cytotoxicity has been found against several class II-negative target cells. However, the interaction of the superantigen with TCR is apparently of low avidity and is usually insufficient to generate a full response (Dohlsten et al., 1991, Herman et al., 1991, and Avery et al., 1994).

Two general categories of superantigens have been described. The soluble exotoxins produced by gram-positive bacteria such as *Staphylococcus aureus* typify bacterially-derived superantigens and are well known for their ability to cause food poisoning and symptoms of shock. Viral superantigens have also been described. In mice, prototypical viral superantigens are encoded by endogenous mouse mammary tumor viruses (MMTVs). These viral superantigens include Mls antigens and are strongly immunogenic for murine T cells.

Because of their ability to stimulate strong T-cell responses in vivo, superantigens have elicited wide interest. M-like proteins of group A streptococci act as a key virulence factor on the bacterial surface. M protein is defined by its antiphagocytic function, whereas M-like proteins, while structurally related to M protein, lack an established antiphagocytic function. The emmL 55 gene, derived from the M stereotype 55 group A streptococci isolate A928, has an amino acid sequence typical of M-like proteins (Boyle et al., 1994, and Boyle et al., 1995).

Bacterial superantigens, when covalently linked to mAbs specific to the cell surface molecules of malignant, MHC II⁻ target cells, can direct lysis of these cells (Dohlsten et al. 1991). It has been demonstrated that conjugation between the superantigen staphylococcal enterotoxin-A (SEA), and mAbs recognizing human colon cancer enabled T cells to lyse colon carcinoma cells in vitro. The use of *Staphylococcal* enterotoxins has been contemplated for cancer vaccines (WO 95/00178).

Immunotherapeutic modalities for the treatment of oncological disorders have been described by a number of scientific investigators. The immunological rejection of tumors has been shown in response to the transfection of tumor cells by such antigens expressed by MHC genes (Hock et al., 1996) and Mycobacterium (Menard et al., 1995). Research into immunotherapy for oncological diseases using MHC antigens and the delivery thereof has been described (EP 569678; WO 95/13092). Other antigens, bacterial and viral, have also been used in combination with cytokine or other immunomodulator gene expression and delivered by means of adenovirus, retrovirus or plasmid vectors (WO 94/21808; WO 96/29093).

BRIEF SUMMARY OF THE INVENTION

The present invention concerns the use of superantigen, such as M-like proteins, expressed by tumor cells as a method for treating oncological disease in an individual or animal. In one embodiment, the method comprises introducing a polynucleotide coding for a superantigen, such as an M-like protein, into a cell such as, for example, a tumor cell, wherein the superantigen is expressed by the transformed cells, and introducing the transformed cells into the patient to be treated. In an exemplified embodiment of the invention, the M-like protein emmL 55 is employed. The emmL 55 gene encodes a polypeptide that has a sequence typical of an M-like protein. In other embodiments, foreign major histocompatibility complex (MHC) genes, such as class II genes, and/or genes encoding cytokines can be inserted and expressed in the cell transformed to express a superantigen.

In one embodiment, genes encoding an M-like protein and a gene encoding a foreign class II MHC are introduced into and expressed in a tumor cell. Polynucleotide molecules encoding proteins contemplated by the subject invention can be used to transform cells either in vitro or in vivo. If the transformation is done in vitro, then the cells expressing the heterologous genes are then implanted into a patient in need of oncological treatment. Polynucleotides encoding M-like protein and MHC class II can be introduced into tumor cells using standard techniques known in the art, such as by electroporation, targeted liposomes, viral vectors and transfection with naked DNA. In vivo transformation of a patients cells can be done using targeted liposomes, viral vectors, direct injection with naked DNA and other methods known in the art.

BRIEF DESCRIPTION OF THE DRAWINGS

FIG. 4 shows a sequence of the pSVK 3/emmL 55 construct (SEQ ID NO. 1). The sequence starts on the pSVK vector and shows the mutation of the ATG start codon which shifts the transcription start site to the second start codon at 761 bp causing deletion of 375 bp of the emmL 55 gene, but does not change the reading frame. The result is an emmL 55 gene (SEQ ID NO. 2) that encodes a truncated form of the emmL 55 protein.

The second sec (SEQ ID NO. 3) shows the partial nucleotide sequence of PSVK 3/emmL 55 construct.

Figure 5:
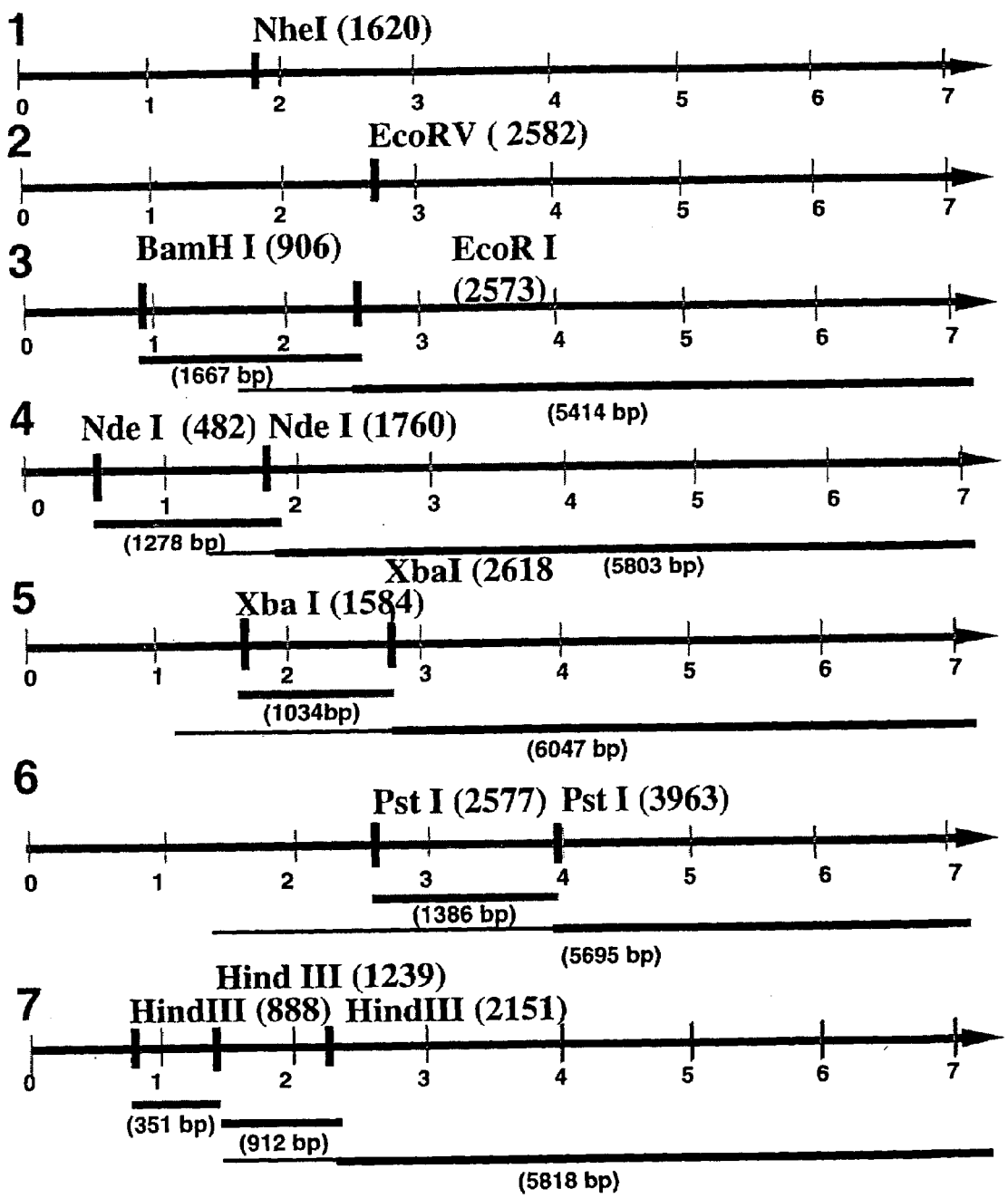

FIG. 5 shows a restriction map of the pcDNA 3/emmL 55.

Figure 6A:
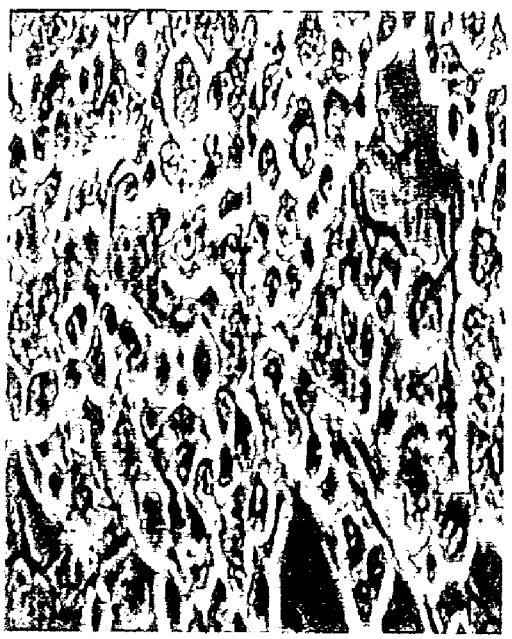
Figure 6B:
Figure 6C:
Figure 6D:

FIGS. 6A–6D show morphology of untransfected or transfected Neuro-2a cell:

FIG. 6A shows Neuro-2a without DNA;

FIG. 6B shows Neuro-2a transfected with MHC II (pcDV 1/α and pcDV 1/β);

FIG. 6C shows Neuro-2a transfected with truncated emmL 55 (pSVK 3/emmL 55);

FIG. 6D shows Neuro-2a transfected with emmL 55 (pCDNA 3/emmL 55).

BRIEF DESCRIPTION OF THE SEQUENCES

SEQ ID NO. 1 shows the nucleotide sequence of a pSVK 3/emmL 55 construct according to the subject invention.

SEQ ID NO. 2 shows the nucleotide sequence of a truncated pSVK 3/emmL 55 construct according to the subject invention.

SEQ ID NO. 3 shows the partial nucleotide sequence of pSVK 3/emmL 55 construct according to the subject invention.

SEQ ID NO. 4 shows an oligonucleotide primer used to amplify an emmL 55 gene according to the subject invention.

SEQ ID NO. 5 shows an oligonucleotide primer used to amplify an emmL 55 gene according to the subject invention.

SEQ ID NO. 6 shows an oligonucleotide primer used to sequence an emmL 55 gene according to the subject invention.

DETAILED DISCLOSURE OF THE INVENTION

The present invention concerns novel methods for treating persons or animals afflicted with oncological disorders, or preventing oncological disorders in persons or animals predisposed to such oncological disorders, such as solid tumors, soft tissue tumors, leukemias, lymphomas and their various metastases and micro metastases. The method comprises providing a patient in need of treatment for an oncological disorder with cells, such as a tumor cells, that has been transformed to express a superantigen protein. In one embodiment, cells are treated so as to introduce a polynucleotide encoding a superantigen protein that will be expressed by the cells, and then providing a patient in need of such treatment with the transformed cells of the invention. In a preferred embodiment, the superantigen is an M-like protein. Preferably, the M-like protein is emmL 55, or a fragment or variant thereof. The expression of full length and truncated versions of the emmL 55 protein in a cell are specifically exemplified.

The subject invention also concerns methods for treating or preventing oncological disease in a human or animal that comprises expressing a polynucleotide coding for a first superantigen in a cell, and further expressing in the cell a second polynucleotide coding for at least one viral, bacterial or eukaryotic protein that is immunogenic or immunostimulatory and providing the human or animal with the transformed cells. In one embodiment, the subject method comprises expressing a superantigen, such as an M-like protein, and a foreign MHC antigen, such as a class II antigen, in a cell and providing a patient with the transformed cells that express superantigen and foreign class II MHC antigen. In another embodiment, the subject method comprises expressing a superantigen and a cytokine on a cell and providing a patient with the transformed cells expressing superantigen and cytokine. A further embodiment of the subject method comprises expressing a superantigen, a foreign MHC antigen and a cytokine in a transformed cell and providing a patient with the transformed cell. Cytokines useful in the subject method include interleukins, such as IL-1, IL-2, IL-3, IL-4, TNFα, IFNα, IFNβ, IFNγ, GM-CSF, MIP1α, MIP1β and TGFβ, and any other suitable cytokines capable of modulating immune response. The expressed cytokines can be either retained on the cell surface or secreted by the cell. In another embodiment of the present invention, the method comprises expressing a superantigen and an antigen or antigen complex, such as those from pigs (Sykes et al., 1991) or Mycobacterium (EP 6571 68), which has been shown to be highly immunogenic, that can induce an acute immune response to the antigen in a xenotransplantation. Al so contemplated within the scope of the subject invention are cells transformed to express polynucleotides encoding agents that are chemotactic for immune cells.

The methods of the subject invention can be used in combination with other therapies that are useful in treating oncological disorders. These include, for example, surgical resection of the tumor, radiotherapy, chemotherapy, and antibody directed anti-tumor therapy, such as tumor-specific antibodies conjugated with toxins. Also contemplated for use in conjunction with the subject invention are cancer therapies, such as dendritic cell cancer vaccines (Banchereau, J., R. M. Steinman, 1998; Gilboa, F. et al., 1998).

The tumor cells used with the subject method can be from the person's or animal's own tumor cells to be treated. Also contemplated for use in the subject invention are cells from sources other than the patient to be treated. The cells can be transformed with polynucleotide molecules encoding superantigens (e.g., M-like proteins), foreign MHC antigens and/or cytokines using standard techniques known in the art. Cells can be transformed either in vivo or in vitro. If the transformation is performed in vitro, then transformed cells expressing polynucleotides according to the subject invention can be reinfused back into the animal or person. For in vivo transformation, the polynucleotides can be delivered to the cells, for example, using targeted liposomes that harbor the polynucleotide molecules. Viral vectors, such as adenovirus, adeno-associated virus, retrovirus, pox virus, herpes virus, plasmids and nucleic acid, can also be used for transforming cells with the polynucleotide molecules encoding the polypeptides of the present invention. Cells can also be transfected using naked DNA, i.e., transfection by direct injection of a tumor with naked DNA encoding proteins useful in the subject methods. Targeted liposomes, viral vectors and naked DNA can also be used in vitro to transform cells.

The subject invention also concerns a cell transformed with a polynucleotide molecule or molecules encoding a superantigen, such as an M-like protein, and, optionally, a foreign MHC antigen, such as class II antigen, and/or a cytokine. In a preferred embodiment, the polynucleotide encodes an emmL 55 polypeptide, or a fragment or variant thereof. Particularly preferred are truncated versions of M-like proteins exemplified herein.

The materials and methods of the present invention can also be employed in combination with cytokine or other immunomodulating therapies. Also contemplated within the scope of the methods of the present invention are cells transformed with other streptococcal superantigens that are expressed on the surface of the cell in conjunction with foreign class II MHC expression.

The subject invention also concerns truncated M-like protein, and the polynucleotides that encode the truncated proteins, wherein the truncated M-like protein exhibits greater levels of expression compared to full length M-like protein when expressed in transformed cells. In a preferred embodiment, the M-like protein is emmL 55. In an exemplified embodiment, a truncated emmL 55 protein comprises the sequence encoded by the emmL 55 gene where the protein coding region starts at the second in-frame ATG codon in the nucleotide sequence of the emmL 55 gene. A truncated version of emmL 55 protein can be produced using the plasmid pSVK3/emmL 55 described herein.

The superantigen, foreign MHC antigen, and cytokine proteins that can be used in the present invention include not only those proteins having the same amino acid sequence as found in nature, including allelic variants, but also includes those variant proteins having mutations such as conservative amino acid substitutions, additions and deletions in the protein sequence, as long as the variant protein retains biological or immunotherapeutic activity.

Oncological disorders that can be treated using the methods and compositions of the present invention include lymphomas; leukemias; carcinomas of the bladder, breast, lung, cervix, colon, kidney, liver, ovary, prostate, pancreas, cartilage, testis, tongue, uterus and thyroid; sarcomas such as those of the pelvis, rhabdomyo (muscle), bone and osteogenic; brain tumors; gliomas; gliobastomas; neuroblastomas; melanoma; hepatomas; medulloblastoma; and Wilm's Tumors.

As is well known in the art, the amino acid sequence of a protein is determined by the nucleotide sequence of the DNA. Because of the redundancy of the genetic code, i.e., a single amino acid can be coded for by more than one coding nucleotide triplet (codon). Accordingly, different nucleotide sequences can code for a particular amino acid sequence. The amino acid sequences of the proteins of the subject invention can be prepared by nucleotide sequences other than the wild-type or native sequences. Functionally equivalent nucleotide sequences encoding the amino acid sequence of these proteins and fragments thereof can be prepared by known synthetic procedures. Accordingly, the subject invention includes such functionally equivalent nucleotide sequences.

Thus, the scope of the subject invention includes not only specific nucleotide sequences exemplified herein, but also all equivalent nucleotide sequences coding for proteins of the invention having substantially the same antigenic, immunogenic, or therapeutic activity.

As used herein the term "foreign MHC antigen" refers to MHC antigens that are distinct from the MHC antigens naturally expressed on the cells of the person or animal. MHC antigens within the scope of the invention include class I, class II and class II antigens.

In an exemplified embodiment of the present invention, a neuroblastoma cell line transformed to express a foreign MHC class II antigen and an M-like protein was prepared and used to treat a mouse strain in which the neuroblastoma arises. The clone Neuro-2a was established from a spontaneous tumor of strain A albino mouse in 1969. This tumor line, designated C1300, arose spontaneously in A/J mice and has been carried in this strain since. Neuro-2a resembles human neuroblastoma in many respects and is commonly used as an experimental model. Tumors quickly appear at the site of inoculation after variable latency periods, which are dependent on the numbers of cells inoculated (see Table 1). Concurrent physical examination demonstrates soft, well vascularized tumors with blood vessel transformation and secondary tumor formation. Histological examination demonstrates that the primary sites of metastasis are the lung and liver.

TABLE 1

Tumorgenicity of neuroblastoma cell line Neuro-2a in syngeneic A/J mice.

| Neuro-2a cells × $10^6$ | Mice injected | Latency (days) | % mice with tumor |
|---|---|---|---|
| 3 | 5 | 7–13 | 100 |
| 1 | 5 | 8–20 | 100 |
| 0.5 | 5 | 10–20 | 80 |
| 0.1 | 5 | 14–28 | 80 |
| 0 | 5 | 0 | 0 |

The pSDV1 and pSVK3 vectors are useful for expression studies in a wide variety of mammalian cell lines. They contain sequences for efficient replication in *E. coli*, an mRNA splice site and polyadenylation signal from SV40 for replication and expression in eucaryotic cell line. The genes for Dw14 α and β currently reside separately on pSDV1, a mammalian expression vector originally designed by Okayama and Berg. These plasmids must be cotransfected in order for the MHC class II-DR4 antigen to be expressed on the cell surface. The use of these constructs acts as a positive control in the transfection and expression in Neuro-2a cells and in the suppression of tumor growth. Production of an expression vector expressing the emmL 55 gene is based on the amplification of the emmL 55 gene by PCR and generation of restriction sites at the ends of the product which will allow subsequent ligation to the multiple cloning site of the pSVK3 expression vector. The resulting PCR fragment was gel-purified and subcloned into the pCRII vector. Restriction mapping confirmed that several clones contained the correctly amplified product. A single clone was used for further study. The restriction endonucleases Hind III and EcoRI were used to excise the PCR product from the pCRII cloning vector, gel-purified, and subcloned into pSVK3.

In order to evaluate the expression on the cell surface of these antigens and to develop stably transfected Neuro-2a cell lines, i.e., Neuro-2a cells expressing both emmL 55 and Dw 14, Neuro-2a cells were electroporated with plasmids containing either the emmL 55 gene or the Dw14 α and β genes as described above. Expression of DW-14 and emmL 55 proteins was analyzed by flow cytometry using monoclonal antibodies. Successfully transfected cells were sorted by FACS and evaluated over time. Within two hours of electroporation, greater than 80% of the Neuro-2a cells cotransfected with Dw 14 α and β genes expressed MHC class II-DR4 antigen on the surface. After 21 days, 50% of the cells still expressed this marker. Approximately 30% of cells transfected with the emmL 55 construct expressed detectable amounts of this antigen on their surface immediately following electroporation, but none was detected after 7 days. Sequence analysis revealed that the emmL 55 construct was missing the 5' ATG codon along with other 5' nucleotides. This presumably occurred during PCR amplification. Thus, it may be preferable to subclone the emmL 55 gene directly from the original plasmid into another expression vector containing a selectable marker as a means to keep selective pressure on the cells to retain the plasmid.

Materials and Methods

Mice

Adult A/J syngeneic female mice were purchased from The Jackson Laboratory (Bar Harbor, Mass.). Mice used in this experiment were seven weeks-old. All mice were housed in sterile cages, fed with sterile food and water ad ubitum, and maintained in a pathogen-free animal facility.

Cell Line

Neuro-2a (American Type Culture Collection, Rockville, Md. USA), a subclone of C1300 murine neuroblastoma was maintained in culture on Iscove's Modified Dulbecco's Medium (IMDM) supplemented with 2 mM L-glutamine, 10% (w/v) fetal bovine serum (FBS) (GIBCO Laboratories, Grand Island, N.Y.), penicillin (100 units/ml) and streptomycin (100 µg/ml). The cells were incubated at 37° C. in a humidified incubator in an atmosphere 5% $CO_2$, in 95% air.

Tumor Cell Inoculation

The cells were prepared for inoculation by gently removing them from 75 $cm^2$-tissue culture flasks with a sterile cell scraper. The cell suspension was harvested by centrifugation at 800×g and the resulting pellet resuspended in incomplete IMDM. A/J mice were inoculated sub-cutaneously (sc) in the right flank with Neuro-2a cells. Each set of five mice were injected with the following cell concentrations: $3\times10^6$, $1\times10^6$, $5\times10^5$, and $1\times10^5$, in 0.2 ml incomplete IMDM. The mice were examined for tumor development every other day. A detailed physical examination was performed, by dissecting the mice after 20 days. Tumors and other tissues were removed from the mice and placed in 10% (w/v) neutral buffered formalin for histological examination (Florida Hospital, Florida Pathology Laboratory, Orlando, Fla.).

Amplification of emmL 55 by the Polymerase Chain Reaction (PCR)

The cDNA for emmL 55 was isolated from the parental vector, pJLA 602, which was kindly provided by Dr. M. Boyle, (Medical College of Ohio, 3000 Arlington Avenue, P.O. Box 10008, Toledo, Ohio 43699). PCR assays were carried out in a 50 µl format for product preparation using the thermocycler Twin Block System (Ericomp, San Diego, Calif.). Each PCR reaction contained the following final concentration of reactants: 100 ng template DNA; 2.5 units Taq-Polymerase (Promega, Madison, Wis.); 1 mM of each primer (Oligo, Wilsonville, Oreg.); 1.75 mM $MgCl_2$ (Promega, Madison, Wis.); 5 µl of 10×PCR buffer (Promega, Madison, Wis.), and 250 mM dNTPs (Pharmacia Biotech, Piscataway, N.Y.). For cloning purposes, the primers contained 5' tags with either an Eco RI or Xho I restriction site. The primers used to amplify the emmL 55 gene and for sequencing the amplified gene products are listed in Table 2. Each assay was overlaid with 50 µl of mineral oil and denatured for 5 min. at 94° C. The reaction mixture was subjected to 35 cycles of 1 min. at 94° C. followed by 1 min. at 60° C., 1 min. at 72° C. and 10 min. at 72° C. PCR products for cloning were combined and concentrated using a Microcon Concentrator-100 (Amicon, Beverly, Mass.). The combined products were then applied to a 1% (w/v) agarose gel and separated by electrophoresis at 50 V for 150 min. The resulting 1.6 kb product representing the amplified emmL 55 gene was extracted from the gel and purified by QIAquick column (Qiagen, Chatsworth, Calif.). The DNA was precipitated by incubating 0.1 volumes of 3 M sodium acetate with 2.5 volume of ethanol at 70° C. for 2 hours followed by centrifugation at 12,000×g for 15 min. Finally, the DNA was resuspended in TE buffer (10 mM Tris, HCL and 1 mM EDTA, pH 8.0) and the yield was analyzed by electrophoresis prior to ligation. Electrophoretic analysis of the PCR yield was performed by applying 4 and 8 µl of the product directly onto a 1% (w/v) agarose gel and compared with the DNA Mass Ladder from Gibco (Grand Island, N.Y.).

Cloning of emmL 55 Gene into the pCR II Vector

The TA cloning kit (Invitrogen, San Diego, Calif.) uses the pCR II vector and provides a quick, one-step cloning strategy for the direct insertion of a PCR product into a plasmid vector. TA cloning works by using a Taq polymerase nontemplate-dependent activity, which adds a single deoxyadenosine (A) to the 3' ends of PCR products and by using the pCR II, a linearized vector which has 3' deoxythmidine (T) residues, allowing efficient ligation.

The amount of PCR product needed to ligate with 50 ng (20 fmoles) of pCR II vector was estimated using the formula below:

$$X_{ng} PCR\ product = \frac{(Y\ bp\ product)(50\ ng\ pCRII\ vector)}{(size\ in\ bp\ of\ the\ pCRII\ vector \approx 3900)}$$

Two ligation reactions using the following final concentrations were set up:
1) for 1:1 (vector:product) reaction, 50 ng of pCR II vector: 20.51 ng of emmL 55 DNA were used;
2) for 1:3 reaction, 50 ng of pCR II vector: 61.53 ng of emmL 55 DNA were used.

1 µl of 10×ligation buffer, T4 DNA ligase (4.0 Weiss units) and $H_2O$ up to 10 µl final volume were used for each ligation reaction. Ligation reactions were incubated overnight at 14° C. and used for transformation of competent One Shot INVαF' E. coli cells, provided in the One Shot competent cell kit.

Transformation of One Shot INVαF' E. coli Competent Cells

Two µl of 0.5 M β-mercaptoethanol (β-ME) were added to 50 µl of One Shot INVαF' competent cells and mixed

TABLE 2

List of oligonucleotides for amplification and sequencing of emmL 55.

| Oligo-nucleotide Designation | Sequence (5' to 3') | Description of Target Site |
|---|---|---|
| (a) | oligonucleotides for amplification of the emmL 55 coding sequence | |
| AS1 | TAG AAT TCA TGG CTA AAA ATA CCA CGA ATA G (SEQ ID NO.4) | 5' end of emmL 55 |
| AS2 | TTC TCG AGT TAG TTT TCT TCT TTG CGT TTG AC (SEQ ID NO.5) | 3' end of emmL 55 |

TABLE 2-continued

List of oligonucleotides for amplification and sequencing of emmL 55.

| Oligo-nucleotide Designation | Sequence (5' to 3') | Description of Target Site |
|---|---|---|
| (b) | oligonucleotide utilized for sequencing the amplified emmL 55 product | |
| AS3 | CAG TTC CGC CCA TTC TTC (SEQ ID NO.6) | 5' portion of pSVK 3/emmL 55 | directly with 2 μl of each ligation reaction, incubated on ice for 30 min. and heat shocked at 42° C. for 30 sec. After transformation, the bacterial cells were grown in 450 μl of SOC medium (2% w/v tryptone, 0.5% w/v yeast extract, 10 mM NaCl, 2.5 mM KCl, 10 mM $MgCl_2$, 10 mM $MgSO_4$ and 20 mM glucose) at 37° C. for 1 hour with vigorous shaking. Fifty μl and 200 μl from each transformation vial were spread on Luria-Bertani (LB), (10 g bacto tryptone, 5 g bacto yeast extract, 10 g NaCl, for 1 liter, pH 7) agar plates containing 50 μg/ml of ampicillin and 40 μg/ml X-Gal and incubated overnight. After incubation, plates were shifted to 4° C. for 24 hours to allow proper color development.

Restriction Analysis of pCR II/emmL 55

Restriction analysis was used to determine the presence and orientation of the emmL 55 insert. Blue-white screening of bacterial clones was performed in order to obtain the clones containing the amplified insert. White colonies were used for cracking gel analysis. Briefly, cells from white colonies were transferred into 5 ml of LB broth supplemented with 50 μg/ml ampicillin and grown overnight aerobically at 37° C. Five hundred μl of bacterial culture were transferred into microcentrifuge tubes and centrifuged for 1 min. at 1500×g. Bacterial pellets were lysed in cracking buffer (1% (w/v) SDS, 2 mM EDTA, 0.4 M sucrose, 0.05 M Tris HCL and 0.01% (w/v) Bromo Phenol Blue) and bacterial lysates were run on a 1% (w/v) agarose gel. Clones which had a 5.5 kb size plasmid were used for further analysis. Preparation of the DNA for restriction analysis from One Shot INVαF' cells was then performed using standard procedures. The bacterial cells were lysed using the alkaline mini-prep technique and the DNA was purified by phenol/chloroform extraction (Sambrook et al., 1989). The recombinant DNA was subsequently digested with the following restriction endonucleases: Eco RI (12 units/μl), Xho I (10 units/μl) in combination (Promega, Madison, Wis.).

Subcloning of emmL 55 into pSVK 3

Figure 1:
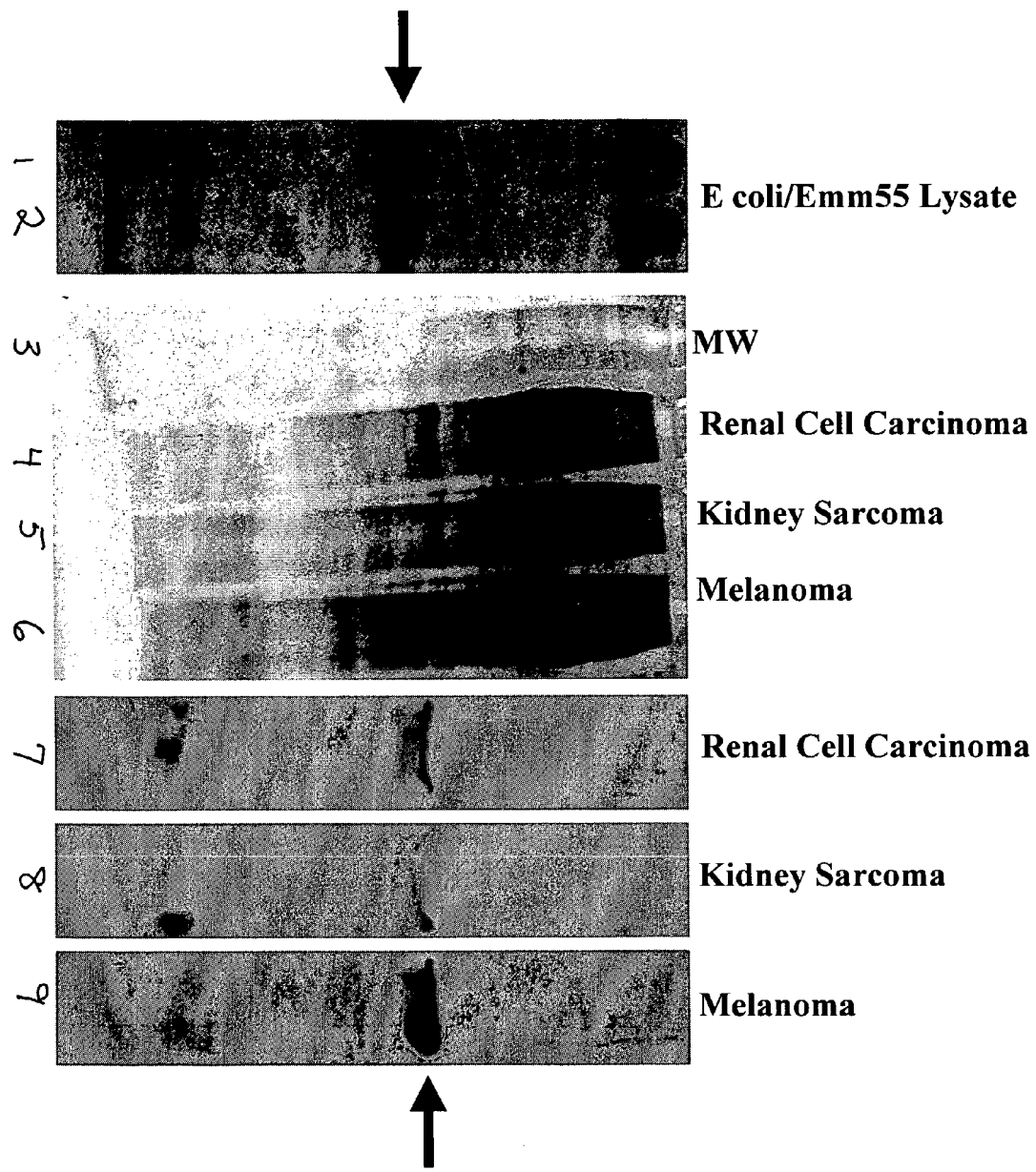
FIG. 1 shows construction of the pSVK 3/emmL 55 expression vector.

To clone emmL 55 into the pSVK 3 plasmid (Pharmacia, Piscataway, N.Y.), emmL 55 cDNA was excised from the pCR II/emmL 55 construct by Eco RI (12 units/μl) and Xho I (10 units/μl) (Promega, Madison, Wis.) (FIG. 1). The digestion was carried out overnight at 37° C. The sample was run on a 1% (w/v) agarose gel at 50 V for 180 min. and the 1.6 kb band was then extracted from the gel and purified using a gel extraction kit (Qiagen, Chatsworth, Calif.) according to the instructions of the supplier. The pSVK3 plasmid (Pharmacia Biotech, Piscataway, N.Y.) was digested with Eco RI (12 units/μl) and Xho I (10 units/μl) in order to produce compatible ends needed for ligation with emmL 55. Restriction enzymes were inactivated by incubation at 70° C. for 20 min. The amount of emmL 55 cDNA needed to ligate with 50 ng of pSVK 3 vector (3919 bp) was estimated using Formula 1. Three ligation reaction were set up using the following final concentrations, for 1:1 (vector:insert) reaction 50 ng:20.41 ng, for 1:3, 50 ng:61.24 ng and for 1:6, 50 ng:122.48 ng of pSVK 3:emmL 55 cDNA, 1 μl of 10×ligation buffer, T4 DNA ligase (4.0 Weiss units) and $H_2O$ up to 10 μl final volume for each ligation reaction.

XL-1 Blue E. coli cells were transformed with the ligation products using a standard heat shock procedure. One hundred μl of ice-cold transformation buffer TMF (10 mM Tris-HCL, 50 mM $CaCl_2$, 10 mM $MgSO_4×7H_2O$, filter sterilized) was added to 200 μl of XL-1 Blue E. coli cells and mixed directly with 2 μl of each ligation reaction, incubated on ice for 45 min. and heat shocked at 37° C. for 2 min. After transformation, the bacteria were left for 10 min. at room temperature, then transferred into 500 μl of LB broth and incubated for 90 min. at 37° C. Twenty five, 50, and 200 μl from each transformation culture were spread on to LB plates supplemented with ampicllin (50 μg/ml) and tetracycline (10 μg/ml) and then incubated overnight at 37° C.

Restriction Map of pSVK 3/emmL 55 Construct

To determine the presence and orientation of the emmL 55 insert, bacterial colonies were isolated and grown overnight in LB broth with 50 μg/ml ampicillin. Four clones were chosen for plasmid isolation and restriction endonuclease analysis. The following endonucleases were used: Bam HI (10 units/μl); Nhe I (12 units/μl); Xho I (10 units/μl) and Eco RI (12 units/μl); Hpa I (10 units/μl) and Cla I (10 units/μl); Hpa I (10 units/μl) and Nhe I (12 units/μl). Clone number 2 was used for further map analysis. A restriction map was constructed using Nhe I (12 units/μl); Nde I (10 units/μl); Pvu II (10 units/μl); Hind III (10 units/μl); Pvu II (10 units/μl) and Nhe I (12 units/μl); Pvu II (10 units/μl) and Nde I (10 units/μl); and Eco RI (12 units/μl) and Xho I (10 units/μl).

Sequence Analysis of pSVK 3/emmL 55

DNA sequence analysis was performed using pSVK 3/emmL 55 as a template. Sequencing was carried out using a sequenase version 1.0 DNA sequencing kit (Amersham, Arlington Heights, Ill.), a C.B.S. SG-500-33 adjustable nucleic acid sequencer and the primers listed in Table 2 according to the Sanger method of dideoxy-mediated chain termination (Sanger et al., 1977). Denaturation of the double-stranded template was carried out by adding 0.1 volumes 2 M NaOH/2 mM EDTA and incubating 30 min. at 37° C. The sample was neutralized by the addition of 0.1 volumes 3 M NaAc, pH 5.5, and the DNA was precipitated as above. The sample was redissolved in 7 μl distilled water. The annealing reaction was carried out by heating the DNA mixture (0.5 μg/μl) with the primers (1 mM) and 2 μl of the reaction buffer at 65° C. for 2 min. After incubation, the reaction was slowly cooled to 35° C. for 15–30 min. To the ice-cold annealed DNA, the following labeling reagents were added: 0.1 M DTT; 0.1 M, 2 μl diluted labeling mix; $^{35}S$ dATP (0.5 μl); and Klenow sequencing polymerase (2 μl). The labeling reaction was carried out by incubating the reagents at room temperature for 2-5 min. The reactions were terminated by adding the labeling reaction (3.5 μl) to the prewarmed A, T, G, C, termination mixtures (2.5 μl) and incubating at 37° C. for 5 min and quenched by adding 4 μl of stop solution. Before loading on a 6% (w/v) sequencing gel, the samples were heated for 2 min. at 75° C. The gel was run at constant power of 35–40 W. After fixing the gel with 10% (w/v) methanol and 10% (w/v) acetic acid, the gel was transferred to 3 MM Whatman paper and placed under vacuum in a dryer for 40 min. at 80° C. The gel was then exposed to X-ray film (Kodak) at room temperature for 24 hours and subsequently developed in Kodak-M35A X-OMAT Processor.

Subcloning of emmL 55 cDNA into pcDNA 3

Figure 2:
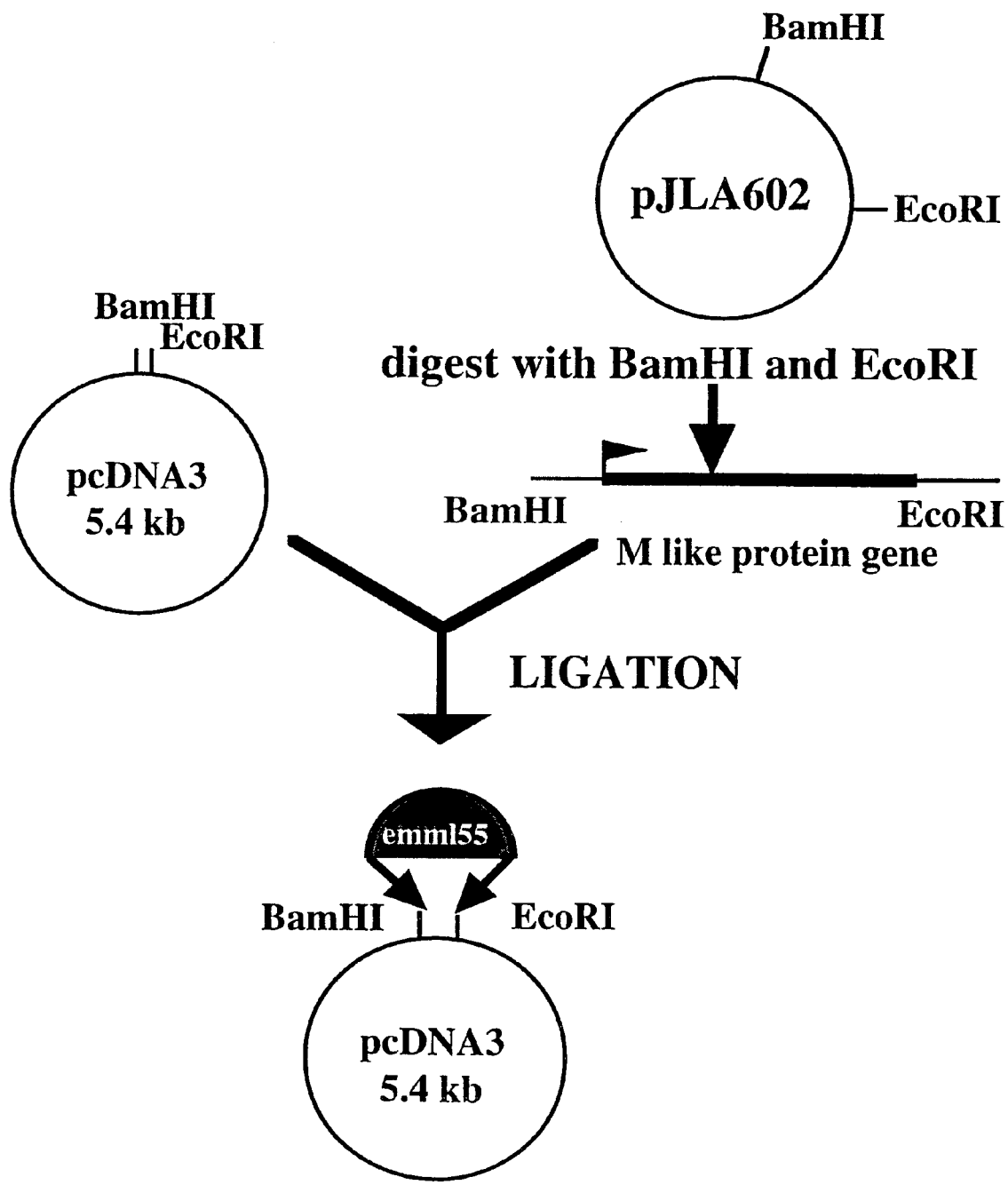
FIG. 2 shows construction of the pcDNA 3/emmL 55 expression vector.

The cDNA for emmL 55 was isolated from the parental vector, pJLA 602, which was kindly provided by Dr. M. Boyle. Isolation and preparation of the parental plasmid from E. coli DH5α was performed using standard techniques (Sambrook et al., 1989). The emmL 55 cDNA for was excised from the pJLA 602 by restriction endonuclease digestion with Bam HI (10 units/μl) and Eco RI (12 units/μl) (FIG. 2). DNA purification was by electrophoresis elution using a QIAquick gel extraction kit (Qiagen, Chatsworth, Calif.). The emmL 55 cDNA was ligated into the pcDNA 3 expression vector (Invitrogen, San Diego, Calif.) which was prepared by double digestion with Bam HI (10 units/μl) and Eco RI (12 units/μl) as above, to reveal the necessary restriction sites.

*E. coli* JM109 high efficiency competent cells (Promega, Madison, Wis.) were transformed with the ligation reaction products which were prepared as follows: The amount of emmL 55 cDNA was estimated using Formula 1. Three ligation reactions were performed for 1:1 (vector:insert) 15.2 ng of emmL 55, for 1:3 45.6 ng of emmL 55.50 ng of pcDNA 3 (5400 bp), T4 DNA ligase (4.0 Weiss units) and $H_2O$ up to 10 μl final volume for each ligation reaction. Reactions were incubated overnight at 14° C. and used for transformation of *E. coli* JM109 high efficiency competent cells. One hundred μl of bacterial cells were mixed with 2 μl of each ligation reaction. After gentle mixing, cells and DNA were incubated on ice for 2 min. and transferred to 42° C. for 1 min. Cultures were then incubated in 1 μl LB broth for 45 min. at 37° C. with shaking. Twenty, 50, and 200 μl of each culture were spread over the surface of LB agar plates supplemented with 50 μg/ml of ampicillin and incubated overnight. Cracking gel analysis was performed and three clones carrying 7,000 bp inserts were studied further.

Restriction Map of pcDNA 3/emmL 55

Preparation of pcDNA 3/emmL 55 DNA for restriction map analysis was performed by the mini-prep alkaline lysis method (Sambrook et al., 1989). Purified DNA from the three selected clones was analyzed by restriction endonuclease digestion with Pst I (10 units/μl), Hind III (10 units/μl) and Xba I (10 units/μl) and agarose gel electrophoresis. A single clone was chosen for the restriction map of pcDNA 3/emmL 55 and was digested with: Nhe I (12 units/μl); Eco RV (20 units/μl); Bam HI (10 units/μl) and Eco RI (12 units/μl); Nde I (10 units/μl); Xba I (10 units/μl); Pst I (10 units/μl); and Hind III (10 units/μl).

Growth Curve of Neuro-2a

Neuro-2a cells were harvested by trypsinization at 37° C. for 5 min. and centrifugation at 800× g for 10 min. at 25° C. Following enumeration by trypan blue exclusion, the cells were serially diluted ($6.4 \times 10^5$, $3.2 \times 10^5$, $1.6 \times 10^5$, $8 \times 10^4$, $4 \times 10^4$, $2 \times 10^4$, $1 \times 10^4$, $5 \times 10^5$, $2.5 \times 10^3$, and $1.2 \times 10^3$), plated in quadruplicate onto 96 well plates and incubated at 37° C., in a humidified atmosphere of 5% $CO_2$ in 95% air for 2, 4, 6, or 8 days. Cell proliferation was measured by the Alamar Blue assay (Alamar Bioscience, Sacramento, Calif.). This assay incorporates a fluorometric/colometric growth indicator which detects metabolic activity. This indicator both fluoresces and changes color in response to a chemical reduction of the growth media resulting from cell growth. Alamar Blue regent was added aseptically to each well in an amount equal to 10% of the cell culture volume (20 μl) and incubated with for 3 hours under cell growth conditions. Absorbency was measured on a Ceres UV 900 HD (Bio Tek Instruments) at a wavelength of 570 nm. Background adsorbance (600 nm) was subtracted prior to tabulating the data.

Inhibition Assay of Neuro-2a With G418

In order to determine the concentration of G418 (Gibco Laboratories, Grand Island, N.Y.) needed for selection of transfected cells, the following experiment was performed. Two cell concentrations ($2 \times 10^4$ and $1.6 \times 10^5$) were chosen and plated onto 96 well plates and G418 at five concentrations (100, 200, 300, 400, and 500 μg/ml) was added. All dilutions were plated in quadruplicate. Replicate plates were incubated at 37° C. in a humidified atmosphere of 5% $CO_2$ on air for 2, 4, 6, 8 or 10 days. Survival was assessed using the Alamar Blue assay as previously described.

Gene Transfer of pcDV 1/α and pcDV 1/β into Neuro-2a by Electroporation

The MHC II cDNA (DR4, DW 14) was generously provided in the Okayama and Berg expression vector, pCDV 1 (Okayama et al., 1987), by Peter K. Gregersen M. D. (North Shore University Hospital, Cornell University Medical College, Manhasset, N.Y.). pcDV 1/α and pcDV 1/β constructs were used for cotransfection of Neuro-2a cells with the MHC II, DR 4 gene. The α gene encodes the α domain of MHC and the β gene encodes for β domain of MHC. The cells were harvested and washed twice with incomplete IMDM. For each electroporation reaction, $2 \times 10^5$/ml of Neuro-2a cells were used. Cell suspension samples of 250 μl were mixed with 250 μl (0.1 μg/μl) each pcDV 1/α and pcDV 1/β DNA in a Gene Pulser Cuvette. The DNA samples were resuspended prior to mixing in 2×Hank's balanced salts buffer (Hbs) (1.4 mM $Na_2HPO_4$, 10 mM KCl, 12 mM glucose, 275 mM NaCl and 40 mM HEPES, pH 7.2). Electroporation was carried out under three conditions: 1000 V, 21 μF; 450 V, 500 μF; and 300 V, 900 μF. After electroporation, the cells were placed on ice for 10 min. then transferred to 6 well plates. The cells were incubated in complete IMDM at 37° C., under 5% $CO_2$. After 24 hours, 3 ml spent medium was replaced with 4 ml fresh medium and the cells were incubated for an additional 48 hours. Gene expression was measured by flow cytometry after 48 hours and after 18 days.

In order to obtain stably transfected cells Neuro-2a cells were electroporated with 20 μg each of pSG1NEOpA, pcDV 1/α and pcDV 1/β at 260 V and 1050 μF. The cells were plated immediately in 5 ml of IMDM and incubated at 37° C. in 5% $CO_2$. After 48 hours, 3 ml spent medium was replaced with fresh 3 ml IMDM and G418 was added to final concentration of 500 μg/ml. G418 was replaced every five days.

Gene Transfer of pSVK 3/emmL 55 into Neuro-2a by Electroporation pSVK 3/emmL 55 was transfected into Neuro-2a cells by electroporation. The Neuro-2a cells were prepared for gene transfer as previously described except that the number of cells used for each reaction was $2 \times 10^6$/ml. pSVK 3/emmL 55 was linearized before transfection with Bam HI (10 units/μl). Twenty μg DNA was resuspended in $H_2O$ and used for each electroporation reaction. Electroporation was carried under three different conditions: 220 V, 1050 μF; 260 V, 1050 μF; and 300 V, 1050 μF. Following electroporation, the cells were plated on the 9 wells culture plates and 5 ml of complete IMDM was added. Gene expression was measured by flow cytometry after 72 hours and 11 days.

In order to obtain stably transfected cells Neuro-2a cells were electroporated with 20 μg each of pSG1NEOpA and pSVK 3/emmL 55 at 260 V and 1050 μF. Cells were cultured under conditions as described for gene transfer of pcDV 1/α and pcDV 1/β.

Gene transfer of pcDNA 3/emmL 55 into Neuro-2a by Electroporation

Twenty μg of pcDNA 3/emmL 55 was electroporated into Neuro-2a cells at concentration of $2 \times 10^6$ cells/ml at 260 V and 1050 μF. The cells were plated immediately in 5 ml IMDM and incubated at 37° C. in 5% $CO_2$ in air. After 48 hours, 3 ml spent medium was replaced with fresh 3 ml IMDM and G418 was added to final concentration of 500 μg/ml. G418 was replaced every five days. The cells was analyzed for expression of emmL 55 by flow cytometry after 21 days.

Analysis of Gene Expression by flow Cytometry

For flow cytometric analysis, the transfected Neuro-2a cells were prepared by gently removing them from the tissue culture flasks with a sterile cell scraper. The cells were washed and collected by centrifugation at 800×g, resuspended in incomplete IMDM to concentration 1×10$^6$ cells/ml. The cells were then incubated for one hour with the primary antibodies at a dilution of 1:500 of antibody:cells. For MHC II expression the primary antibody (anti-MHC-DR-FITC) was purchased from Becton Dickinson (San Jose, Calif.). After washing, fluorescence of the antibody-exposed cells was analyzed by an Epics Elite ESP (Coulter Electronics, Hialeah, Fla.).

Anti-M-like protein antibody (polyclonal α II o and monoclonal 8 F-10; 25 C; and 15 β3) were provided by Dr. M. Boyle (Boyle et al., 1994, and Boyle et al., 1995). After staining with primary antibody the cells were washed three times in incomplete medium then incubated in the presence of a Avidin FITC conjugate for polyclonal α II o or with mouse IgG-FITC (Becton Dickinson San Jose, Calif.) for the monoclonals at 1:1000 (secondary conjugate: cells) at 4° C. in the dark for 30 min. The exposed cells were washed three times, resuspended in a volume of 0.5 ml of incomplete IMDM, then analyzed by flow cytometry. Immunoflourescence background was measured by comparing the staining of untransfected Neuro-2a with both the primary and secondary conjugate and secondary conjugate alone.

Following are examples which illustrate materials and procedures for practicing the invention. These examples are intended for illustrative purposes only and should not be construed as limiting.

EXAMPLE 1

Tumorgenicity of Neuro-2a in A/J Syngeneic Mice

Neuroblastoma cells were highly tumorigenic in A/J syngeneic mice. Visible tumors appeared at the site of inoculation after a variable latency period. The duration of latency was dependent upon the number of cells injected (Table 1). Injection of 3×10$^6$ and 1×10$^6$ cells caused tumor formation in 100% of the mice tested, and in these cases, the latency period was 7–20 days. Eighty percent of the mice injected with 5×10$^5$ and 1×10$^5$ cells developed tumors within 10–28 days. Once the tumors appear, they grew rapidly and their size was not dependent on number of cells originally injected.

The tumors grew under the skin, invaded the surrounding muscle tissue and approached 75% of the weight of the mouse. Resected tumors were soft and well vascularized; angiogenesis of blood vessels was evident. Additionally, in some mice secondary tumor formation was observed. The overwhelming size of the malignant tissue caused necrosis in some of the tumors examined, but on physical examination, there were no neoplasms apparent in other tissues (lung, liver, spleen, bone marrow). Histological examination, however, showed that the metastasis had occurred with microscopic, neoplastic foci being present in the lung and the liver, but not in the spleen or bone marrow.

EXAMPLE 2

Construction and Analysis of the pCR II/emmL 55

In order to subclone the emmL 55 gene into pSVK 3, emmL 55 was amplified from the parental vector, pJLA 602 and restriction sites necessary for subcloning were added to the ends of the amplified product. Agarose gel electrophoresis of the emmL 55 PCR product showed that the size of amplified gene was 1.6 kb and the amount of the amplified product was 8 ng per 1 μl of the TE buffer.

One Shot INFVαF' E coli. competent bacterial cells were then transformed with pCR II/emmL 55. Bacterial clones were screened for the presence of the recombinant construct by white/blue selection. One clone showed the expected size 5.5 kb and was chosen for restriction analysis. The pCR II/emmL 55 construct, when digested with Eco RI and Xho I restriction enzymes, released the emmL 55 gene. Agarose gel electrophoresis of the digested product show the expected band pattern, 1.6 kb for emmL 55 and 3.9 kb for the pCR II vector. The amplified emmL 55 gene was used for further cloning into the pSVK 3 expression vector.

EXAMPLE 3

Construction and Analysis of pSVK 3/emmL 55

Figure 3:
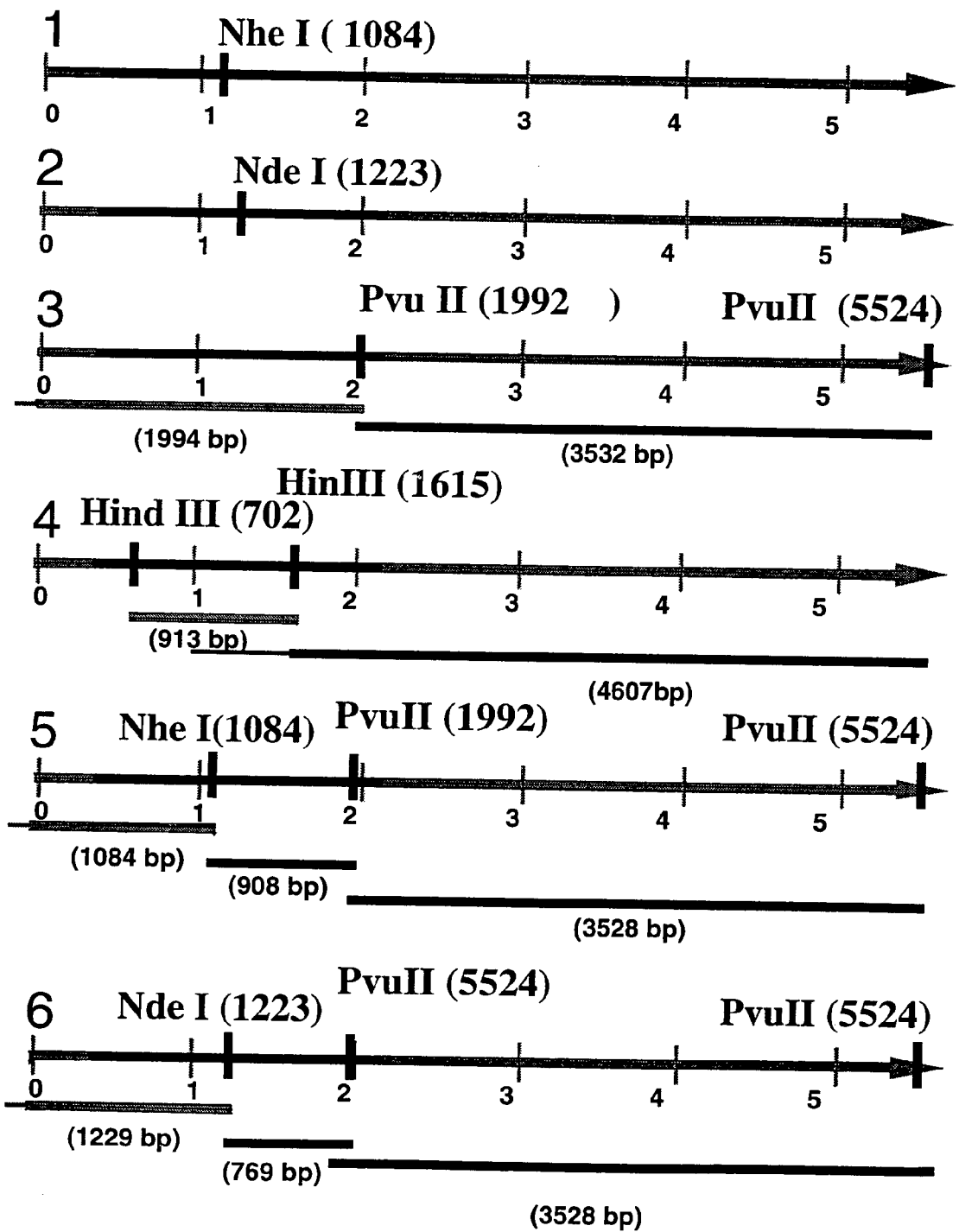
FIG. 3 shows a restriction map of the pSVK 3/emmL 55.

From the 20 analyzed bacterial clones, transformed with the pSVK 3/emmL 55, four clones with 5.5 kb size were selected and digested with restriction enzymes. Three out of four clones transformed with pSVK 3/emmL 55 exhibited the expected banding pattern and one was used for the subsequent analysis. pSVK 3/emmL 55 when digested with Nhe I and with Nde I generated a 5.5 kb band as expected. Digestion with Pvu II yielded a 2 kb and a 3.5 kb band and digestion with Hind III generated two bands, 0.9 kb and 4.6 kb. Double digestion with Pvu II and Nhe I resulted in three bands of approximately 1 kb, 2 kb and 5.5 kb pairs and digestion with Pvu II and Nde I generated three bands, 0.77 kb, 1.2 kb, and 3.5 kb (FIG. 3). Restriction analysis of pSVK 3/emmL 55 revealed that the recombinant construct had the expected size (5.5 kb) and the expected map.

In order to confirm that the correct product was amplified, sequence analysis was performed. The partial sequence of the emmL 55 gene and the pSVK 3 vector was determined and is presented in FIG. 4. The analyzed gene exhibited the typical sequence of emmL 55. However, because of a mutation in the sequence at the site of the first start codon the transcription start site was shifted to the second ATG codon at 761 bp position of the emmL 55 gene and the expressed recombinant protein was truncated (FIG. 4, the second start codon is at 761 bp site of pSVK 3/emmL 55.

EXAMPLE 4

Construction and Analysis of the pcDNA 3/emmL 55

FIG. 5 shows results from the restriction analysis of pcDNA 3/emmL 55. The digestion of three clones with Hind III and Pst I in separate reactions yielded the expected band sizes. One of these clones was analyzed by the subsequent restriction analysis. The recombinant plasmid was linearized by Eco RV, which recognizes a site in pcDNA 3 and by Nhe I, which recognizes a site in emmL 55. Digestion with Bam HI and Eco RI yielded a 1.6 kb and a 5.4 kb fragment. Nde I recognizes a site the expression vector backbone and in the emmL 55 gene, generating two bands (1.3 kb and 5.8 kb). There are two Pst I sites present in pcDNA 3 and restriction with this enzyme generated two fragments (1.4 kb and 5.7 kb bands). Hind III generates three bands 351 bp, 912 bp and 5818 bp. The restriction digests of the pcDNA 3/emmL 55 construct and agarose gel electrophoresis confirm the identity of this plasmid. It was concluded that the recombinant plasmid could be used for the transfection of the Neuro-2a cells.

EXAMPLE 5

Growth Characteristics of Neuro-2a

Cell proliferation assays were performed to estimate the growth characteristics of the Neuro-2a cells needed for subsequent experiments. Ten starting cell concentrations were continuously incubated over an 8 day period with cell numbers being determined every other day. Cell proliferation was measured using Alamar Blue. Results were expressed as a mean of Alamar Blue adsorbance of four cultures plus or minus standard error. The lower cell concentrations, up to $1 \times 10^4$ cells/ml showed standard growth characteristics. In higher concentrations, between $2 \times 10^4$ and $4 \times 10^4$ cells/ml, cells grew exponentially for the first four days then reached stationary phase and started to die. Exponential growth was observed in concentrations between $8 \times 10^4$ and $1.6 \times 10^5$ cells/ml for the first two days and the viable count decreased slowly in the following days. Two cell concentrations: $2 \times 10^4$ and $1.6 \times 10^5$ cells/ml were chosen for use in for the drug sensitivity assay.

EXAMPLE 6

Drug Sensitivity Assay

A drug sensitivity assay was performed to establish the concentration of G418 needed for killing Neuro-2a cells. Cell death was measured by the Alamar Blue assay. The growth of Neuro-2a cells ($2 \times 10^4$ cells/ml) was efficiently suppressed by 500 μg/ml of G418. This concentration of the toxic agent caused growth inhibition of up to 78% after 2 days and the viability of cells dropped to zero after 6 days. Growth of Neuro-2a was also inhibited at concentrations of 400 and 300 μg/ml, while concentrations of 100 and 200 μg/ml of G418 had minimal effect on cell growth.

Similar patterns of the growth inhibition by G418 were noted when cell concentration was $1.6 \times 10^5$ cells/ml. In this experiment the most efficient inhibition of cell growth was observed when 500 μg/ml of drug was used. From these results it was concluded that 500 μg/ml is an effective amount of G418 for selecting stably transfected Neuro-2a cells.

EXAMPLE 7

Morphological Characteristics of Stable Transfected Cell Lines

Introduction of the vectors into cells changed the cell morphology (FIG. 6). The transfected cells selected by G418 (panels B, C, and D) grew in characteristic clumps, whereas the untransfected neuroblastoma cells formed an even monolayer (panel A). This finding can not be explained by the presence of G418 in the medium since in previous experiments (inhibition assay) Neuro-2a did not show any morphological changes in the presence of drug.

EXAMPLE 8

Expression of MHC Class II Antigen by Neuro-2a Cells

Using flow cytometry, it was found that the recombinant antigen, DR 4, DW 14 (MHC II) was successfully expressed by Neuro-2a cells. Forty eight hours after electroporation, up to 84.8% of the cells were able to express the recombinant antigen. The expression of the DR 4, DW 14 antigen was still present 18 days after electroporation. Twenty nine to 48.2% of the Neuro-2a cells were able to bind mAbs against DR 4, DW 14 after 18 days.

It was also observed that the level of DR 4 expression was dependent on the electroporation conditions. In a second independent experiment, up to 55.1% of Neuro-2a cells was able to express the recombinant antigen 48 hours after electroporation (Table 3). The highest level of fluorescence was observed in cells transfected at 1000 V and 21 μF. Fifty three % of cells expressed MHC 1'-DR 4 antigen when they were electroporated at 50 V, 500 μF and 33.2% of cells expressed the antigen when they were transfected at 300 V and 900 μF.

TABLE 3

| Expression of MHC II-DR 4 and truncated emmL 55 by Neuro-2a cells | | | | | | |
|---|---|---|---|---|---|---|
| Electroporation conditions | 220 V 1050 μF | 260 V 1050 μF | 300 V 1050 μF | 300 V 900 μF | 450 V 500 μF | 1000 V 21 μF |
| Expression of MHC II-DR4 | NA | NA | NA | 33.2% | 53.2% | 55.1% |
| Expression of truncated emmL 55 | 7% | 35% | 20.4% | NA | NA | NA |

EXAMPLE 9

Expression of Truncated emmL 55 Gene in Neuro-2a Cells

Flow cytometry was used to determine the efficiency of transfection of Neuro-2a cells with the pSVK 3/emmL 55 construct. The cells demonstrated moderate expression of the truncated emmL 55 gene (Table 3). Seventy two hours after 35% of the cells exhibited the immunofluorescence using polyclonal antibodies when electroporated at 260 V and 1050 μF transfection, 20.4% at 300 V and 1050 μF and 7% at 220 V and 1050 μF. Eleven % of Neuro-2a cell was able to express the recombinant protein 11 days after electroporation.

EXAMPLE 10

Stable Expression of Full Length emmL 55 Truncated emmL 55 and MHC II in Neuro-2a Cells The murine neuroblastoma cell line was transfected with the pcDNA 3/emmL 55 construct containing the complete emmL 55 gene. The surface expression of the transfected genes was confirmed by flow cytometry using the 8 F-10 mAb. Twenty one days after electroporation, 10% of the transfected Neuro-2a cells kept under G418 selection were able to bind the 8 F-10 antibody.

For stable expression, Neuro-2a cells were cotransfected with pSG1NeopA and pSVK 3/emmL 55 plasmid at 260 V and 1050 μF and kept in culture with G418 for several weeks. Since these conditions were the most efficient in previous electroporations, they were used then for the electroporation of Neuro-2a with the pcDV 1/α pcDV 1/β and pSG1NeopA. Stably transfected cells were kept in culture under G418 selection for several weeks.

It should be understood that the examples and embodiments described herein are for illustrative purposes only and that various modifications or changes in light thereof will be suggested to persons skilled in the art and are to be included within the spirit and purview of this application and the scope of the appended claims.

REFERENCES

EP 569678
WO 95/13092
WO 94/21808
WO 96/29093
WO 95/00178

Avery, A. C. et al. (1994) Activation of T cells by superantigen in Class II-negative mice. *J. Immunol.* 153: 4855–4861.

Banchereau, J., R. M. Steinman (1998) Dendritic cells and the control of immunity. *Nature* 392: 245–252.

Boyle, M. D. P. et al. (1994) Analysis of gene encoding two unique type IIo immunoglobulin G-binding proteins expressed by single group A Streptococcal isolate. *Infection and Immunity* 62: 1336–1347.

Boyle, M. D. P. et al. (1995) Characterization of a gene coding for a type IIa bacterial IgG-binding protein. *Mol. Immunology* 9: 669–678.

Dellabona, P., J. Peccoud, J. Kappler (1990) Superantigens interact with MHC Class II molecules outside of the antigen groove. *Cell* 62: 1115–1121.

Dohlsten, M. et al. (1991) Monoclonal antibody-targeted superantigens: A different class of anti-tumor agents. *Proc. Natl. Acad. Sci.* 88: 9287–9291.

Dohlsten, M. et al. (1991) Human MHC Class II-negative colon carcinoma cells present Staphylococcal superantigens to cytotoxic T lymphocytes: evidence for a novel enterotoxin receptor. *Eur. J. Immunol.* 21:1229–1233.

Fleischer, B., U. Hartwig (1992) T-lymphocyte stimulation by microbial superantigens. *Chem. Immunol.* 55: 36–64.

Fraser, J. D., M. E. Newton, A. Weiss (1992) CD28 and T cell antigen receptor signal transduction coordinately regulate interleukin-2 gene expression in response to superantigen stimulation. *J. Exp. Med.* 175: 1131–1134.

Gilboa, E., S. K. Nair, H. K. Lyerly (1998) Immunotherapy of cancer with dendritic-cell-based vaccines. *Cancer Immunology and Immunotherapy* 46(2): 82–87.

Hartwig, U. F., B. Fleischer (1993) Mutations affecting MHC Class II binding of the superantigen streptococcal erythrogenic toxin. *Int. Immunol.* 5: 869–875.

Herman, A. et al. (1991) Identification of the staphylococcal enterotoxin A superantigen binding site in the β1 domain of the human histocompatibility antigen HLA-DR. *Proc. Natl. Acad. Sci. USA* 88: 9954–9958.

Herrmann, T. et al. (1991) Staphylococcal enterotoxin-dependent lysis of MHC Class II-negative target cells by cytolytic T lymphocytes. *J. Immunol.* 146: 2504–2512.

Hock, R. A. et al. (1996) Murine neuroblastoma vaccines produced by retroviral transfer of MHC class-II genes; major histocompatibility complex class-II gene transfer to mouse cell culture using a retro virus vector, for cancer gene therapy. *Cancer Gene Ther.* 3(5): 314–320.

Johnson, H. M., J. K. Russell, C. H. Pontzer (1992) Superantigens in human disease. *Scientific American* (April): 92–101.

Karp, D. R. et al. (1990) The alpha 1 domain of the HLA-DR molecule is essential for high-affinity binding of the toxic shock syndrome toxin-1. *Nature* 346: 474–476.

Menard, S. et al. (1995) Mycobacterium tuberculosis gene transfer in melanoma cells induces antitumoral immunity in mice; tumor-associated antigen gene transfer and expression in melanoma cell culture for cancer immunotherapy. *Cancer Gene Ther.* 2(4): 318.

Mollick, J. A. et al. (1991) Staphylococcal exotoxin activation of T cells: Role of exotoxin-MHC Class II binding affinity and Class II isotype. *J. Immunol.* 146: 463–468.

Okayama, H. et al. (1987) High efficiency cloning of full-length cDNA: construction and screening of cDNA expression libraries for mammalian cells. *Methods in Enzymology* 154: 3–28.

Panina Bordignan, P. et al. (1992) Identification of HLA-DR alpha chain residues critical for binding of the toxic shock syndrome toxin superantigen. *J Exp Med.* 176: 1779–1784.

Rust, C. J. et al. (1990) Specific recognition of Staphylococcal enterotoxin A by human T cells bearing receptors with the Vγ9 region. *Nature* 346: 572–574.

Sambrook, J., E. F. Fritsch, T. Maniatis (1989) *Molecular cloning: A laboratory manual.* Cold Spring Harbor Laboratory Press, Cold Spring Harbor, N.Y.)

Sanger, F., S. Niklen, R. A. Coulson (1977) DNA sequencing. *Proc Nat Acad Sci.* 74: 5463–5467.

Webb, S. R., N. R. J. Gasoigne (1994) T-cell activation by superantigens. *Curr Opinion in Immun.* 6: 467–475.

We claim:

1. An isolated cancer cell transformed with an expression vector comprising a promoter operably linked to a nucleic acid encoding emmL55 polypeptide wherein the nucleic acid comprises SEQ ID NO: 1.

2. The cancer cell of claim 1 which is a neuroblastoma cell.

3. The neuroblastoma cell of claim 2 wherein the emmL 55 polypeptide is surface-expressed.

4. The cancer cell of claim 1 further further comprising a second expression vector encoding a foreign MHC II antigen.

5. The cancer cell of claim 4 wherein the MHC II antigen is UR4 DW14 polypeptide.

6. The cancer cell of claim 4 wherein the MHC II antigen is expressed in the cell.

7. The cancer cell of claim 4 wherein the MHC II antigen is expressed on the cell surface.

8. The cancer cell of claim 4 which is a neuroblastoma cell.

9. A cell line prepared by culturing and propagating the neuroblastoma cell of claim 2.

10. An isolated mammalian cancer cell transformed with an expression vector comprising a promoter operably linked to a nucleic acid encoding emmL 55 polypeptide wherein the nucleic acid comprises SEQ ID NO: 1.

11. The mammalian cancer cell of claim 10 which is a human cell.

12. The mammalian cancer cell of claim 11 which is a human cancer tumor cell.

13. The mammalian cancer cell of claim 12 wherein the human cancer tumor cell is a neuroblastoma cell.

14. An isolated mammalian cancer cell transformed with an expression vector comprising a promoter operably linked to a nucleic acid having the sequence of SEQ ID NO: 1 from postion 761 to position 850.

15. A cell line prepared by culturing and propagating the cancer cell of claim 4 or claim 5.

* * * * *

UNITED STATES PATENT AND TRADEMARK OFFICE
CERTIFICATE OF CORRECTION

PATENT NO.         : 7,094,603 B2
APPLICATION NO. : 10/652578
DATED                  : August 22, 2006
INVENTOR(S)        : Michael J.P. Lawman and Patricia Lawman It is certified that error appears in the above-identified patent and that said Letters Patent is hereby corrected as shown below:

Column 4,
Line 9, "use of superantigen" should read -- use of superantigens --.
Line 57, "PSVK 3/emmL SS construct" should read -- pSVK 3/emmL SS construct --.

Column 5,
Line 30, "such as a tumor cells, that has been" should read -- such as tumor cells, that have been --.

Column 6,
Lines 3-4, "Al so contemplated" should read -- Also contemplated --.

Column 7,
Line 15, "gliobastomas" should read -- glioblastomas --.
Line 41, "class I, class II, and class II antigens" should read -- class I, class II, and class III antigens --.

Column 8,
Line 16, "eucaryotic cell line" should read -- eukaryotic cell line --.
Line 38, "Dw 14" should read -- Dw14--.
Line 39, "DW-14" should read -- Dw14--.
Line 45, "Dw 14" should read -- Dw14--.

Column 11,
Line 53, "Three litigation reaction were" should read -- Three litigation reactions were --.

Column 12,
Lines 61-62, "for was excised" should read -- was excised --.

Column 14,
Lines 45-46, "Electroporation was carried under" should read -- Electroporation was carried out under --.

Column 18,
Lines 9-10, "cells was able to express" should read -- cells were able to express --.
Line 13, "expressed MHC 1'-DR 4 antigen" should read -- expressed MHC II-DR 4 antigen --.

UNITED STATES PATENT AND TRADEMARK OFFICE
CERTIFICATE OF CORRECTION

| | |
|---|---|
| PATENT NO. | : 7,094,603 B2 |
| APPLICATION NO. | : 10/652578 |
| DATED | : August 22, 2006 |
| INVENTOR(S) | : Michael J.P. Lawman and Patricia Lawman |

It is certified that error appears in the above-identified patent and that said Letters Patent is hereby corrected as shown below:

<u>Column 24</u>
Line 42, "postion 761" should read -- position 761 --.

Signed and Sealed this

Twenty-sixth Day of June, 2007

JON W. DUDAS
*Director of the United States Patent and Trademark Office*